US011246521B2

(12) United States Patent
Takenaka et al.

(10) Patent No.: US 11,246,521 B2
(45) Date of Patent: Feb. 15, 2022

(54) METHOD FOR EVALUATING MUSCULAR STRENGTH CHARACTERISTICS

(71) Applicant: Honda Motor Co., Ltd., Tokyo (JP)

(72) Inventors: Toru Takenaka, Saitama (JP); Yasushi Ikeuchi, Saitama (JP); Hiroshi Uematsu, Saitama (JP); Koji Akatsuka, Saitama (JP); Tomoyuki Shimono, Kanagawa (JP); Takahiro Fujishiro, Kanagawa (JP); Yu Goto, Kanagawa (JP)

(73) Assignee: Honda Motor Co., Ltd., Tokyo (JP)

( * ) Notice: Subject to any disclaimer, the term of this patent is extended or adjusted under 35 U.S.C. 154(b) by 245 days.

(21) Appl. No.: 16/505,636

(22) Filed: Jul. 8, 2019

(65) Prior Publication Data

US 2020/0060600 A1 Feb. 27, 2020

(30) Foreign Application Priority Data

Aug. 27, 2018 (JP) .............................. JP2018-158227

(51) Int. Cl.
*A61B 5/22* (2006.01)
*A61B 5/00* (2006.01)
*A61B 5/11* (2006.01)

(52) U.S. Cl.
CPC ............ *A61B 5/224* (2013.01); *A61B 5/1107* (2013.01); *A61B 5/4528* (2013.01);
(Continued)

(58) Field of Classification Search
CPC ....... A61B 5/0048; A61B 5/221; A61B 5/224; A61B 5/4528; A61B 5/6824;
(Continued)

(56) References Cited

U.S. PATENT DOCUMENTS

| 2008/0202232 | A1 | 8/2008 | Kadota | |
|---|---|---|---|---|
| 2008/0288107 | A1* | 11/2008 | Tokita | B25J 9/104 700/245 |
| 2010/0050765 | A1* | 3/2010 | Kadota | A61B 5/6828 73/379.01 |

FOREIGN PATENT DOCUMENTS

| CN | 102065766 | 5/2011 |
|---|---|---|
| JP | 2000210272 | 8/2000 |

(Continued)

OTHER PUBLICATIONS

Tojo, Naoya, et al. "Estimation of Antagonistic Output Ratios Based on Force Distribution at End Effector of Limb" Feb. 2017, IEEE Transactions on Industrial Electronics, vol. 64, 1783-1792 (Year: 2017).*

(Continued)

*Primary Examiner* — Christian Jang
*Assistant Examiner* — Anna Roberts
(74) *Attorney, Agent, or Firm* — JCIPRNET

(57) ABSTRACT

Provided is a method for evaluating muscle strength characteristics of a limb based on a muscle group model including a first pair of antagonistic one-joint muscles, a second pair of antagonistic one-joint muscles, and a pair of antagonistic two-joint muscles, where the limb has a first rod having a proximal end supported by a first joint and a second rod supported on a free end of the first rod through a second joint. The method includes: measuring a maximum output of a free end of the second rod in at least one predetermined direction; measuring orbiting outputs of the free end of the second rod in all directions in the plane; and creating a hexagonal maximum output distribution corresponding to a contribution amount of each muscle of the muscle group model based on the maximum output in the predetermined direction and the orbiting outputs.

5 Claims, 13 Drawing Sheets

(52) U.S. Cl.
CPC .......... *A61B 5/6824* (2013.01); *A61B 5/6831* (2013.01); *A61B 5/7253* (2013.01)

(58) Field of Classification Search
CPC ... A61B 5/6831; A61B 5/7253; A61B 5/1107; A61B 5/1121
USPC .......................................................... 600/587
See application file for complete search history.

(56) References Cited

FOREIGN PATENT DOCUMENTS

| JP | 2008206889 | | 9/2008 |
|---|---|---|---|
| JP | 2015077397 | | 4/2015 |
| JP | 2017035374 A | * | 2/2017 |
| TW | 201113005 | | 4/2011 |

OTHER PUBLICATIONS

Tojo, Naoya and Shimono, Tomoyuki, "An Estimation Method of Antagonistic Ratios of Functional Effective Muscles of Upper Limb Based on Maximum Force Distribution at End-Effector" 2014, IEEE (Year: 2014).*

Toru Oshima, et al., "Effective muscle strength evaluation for respective functions using muscle coordinate system including one-joint muscles and two-joint muscles—Simple measurement method of output distribution," Journal of the Japan Society for Precision Engineering, vol. 67, Jan. 2001, pp. 944-948.

Office Action of Japan Counterpart Application, with English translation thereof, dated Mar. 31, 2020, pp. 1-6.

Office Action of China Counterpart Application, with English translation thereof, dated Dec. 22, 2021, pp. 1-14.

* cited by examiner

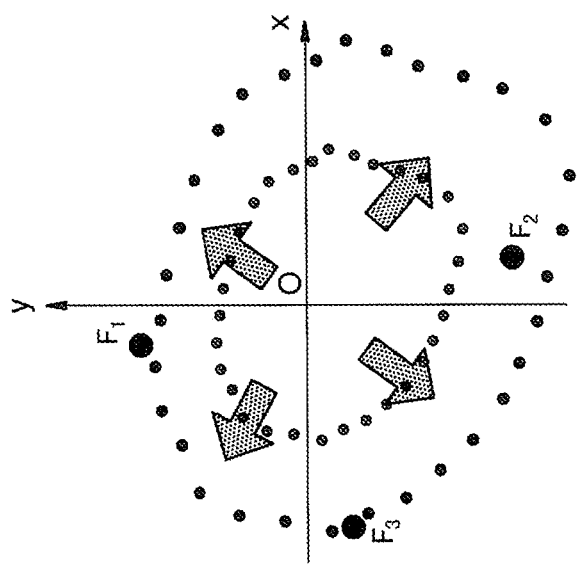
FIG. 14C
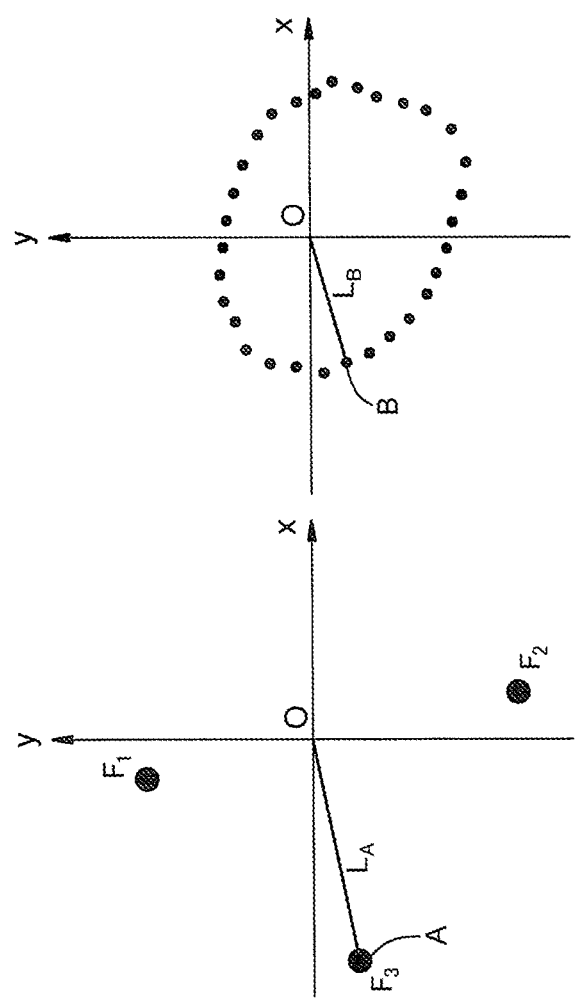
FIG. 14B
FIG. 14A

US 11,246,521 B2

METHOD FOR EVALUATING MUSCULAR STRENGTH CHARACTERISTICS

CROSS REFERENCE TO RELATED APPLICATIONS

This application claims the priority benefit of Japanese Patent Application No. 2018-158227, filed on Aug. 27, 2018. The entirety of the above-mentioned patent application is hereby incorporated by reference herein and made a part of this specification.

BACKGROUND

Technical Field

The disclosure relates to a method for evaluating muscular strength characteristics that evaluates muscular strength characteristics of limbs of a human or an animal.

Description of Related Art

As a model for evaluating muscles contributing to movement in a two-dimensional plane of a limb including two joints such as an upper limb or a lower limb, a 3-pair of 6-muscle model in which muscles provided in the limb are classified into a first pair of antagonistic one-joint muscles, a second pair of antagonistic one-joint muscles, and a pair of antagonistic two-joint muscles is known (for example, Non Patent Document 1: OSHIMA Tom, FUJIKAWA Tomohiko, KUMAMOTO Minayori, "Effective muscle strength evaluation for respective functions using muscle coordinate system including one-joint muscles and two muscles-Simple measurement method of output distribution", Journal of the Japan Society for Precision Engineering, Vol. 67, No. 6, p. 943-948 (2001)). In the 3-pair of 6-muscle model, a maximum output which can be exerted at a tip of the limb is represented by a hexagonal maximum output distribution in which maximum outputs of each muscle are summed.

A method for evaluating muscle strength characteristics which evaluates muscle strength characteristics of a subject based on the 3-pair of 6-muscle model is known (for example, Patent Document 1: Japanese Application Laid-open No. 2000-210272). In Patent Document 1, the maximum output distribution is obtained based on a predetermined output in four directions in the two-dimensional plane (a four-point measurement method). Further, in Patent Document 1, the maximum output of each muscle is calculated based on the maximum output distribution, and the calculated maximum output of each muscle is used for muscle strength evaluation in rehabilitation treatments or sports, training instruction evaluation, and the like.

In the four-point measurement method described in Patent Document 1, since the hexagonal maximum output distribution is obtained based on the maximum output in the four directions, the number of points of data is small and thus reproducibility and reliability of the obtained maximum output distribution are poor.

In view of above, the disclosure provides a method for evaluating muscle strength characteristics which has excellent reproducibility and reliability in an obtained maximum output distribution.

SUMMARY

According to one aspect of the disclosure, a method for evaluating muscle strength characteristics is provided. The muscle strength characteristics of a limb are evaluated based on a muscle group model including a first pair of antagonistic one-joint muscles that straddle the first joint, a second pair of antagonistic one-joint muscles that straddle the second joint, and a pair of antagonistic two-joint muscles that straddle both the first and the second joints, where the limb has a first rod having a proximal end supported by a first joint and a second rod supported on a free end of the first rod through a second joint. The method includes: measuring a maximum output of a free end of the second rod in at least one predetermined direction in a plane defined by the first and the second rods; measuring orbiting outputs of the free end of the second rod in all directions in the plane; and creating a hexagonal maximum output distribution corresponding to a contribution amount of each muscle of the muscle group model based on the maximum output in the predetermined direction and the orbiting outputs.

BRIEF DESCRIPTION OF THE DRAWINGS

FIGS. 14A-14C are explanatory views for explaining a modified example of a method for calculating a magnified orbiting output.

DESCRIPTION OF THE EMBODIMENTS

In the following, a method for evaluating muscle strength characteristics according to the disclosure will be described with reference to the drawings for two exemplary embodiments used to evaluate muscle strength characteristics of a right upper limb of a person.

First Embodiment

A method for evaluating muscle strength characteristics is based on a known 3-pair of 6-muscle model. The 3-pair of 6-muscle model is a model of a muscle which contributes to an output at a tip (a carpal joint portion, a tarsal joint portion) of a limb in two-dimensional movement of a limb including two joints (a shoulder joint and an elbow joint, a hip joint and a knee joint) such as an upper limb or a lower limb. Hereinafter, the 3-pair of 6-muscle model will be described in the scope necessary for the embodiment of the disclosure.

Figure 1:
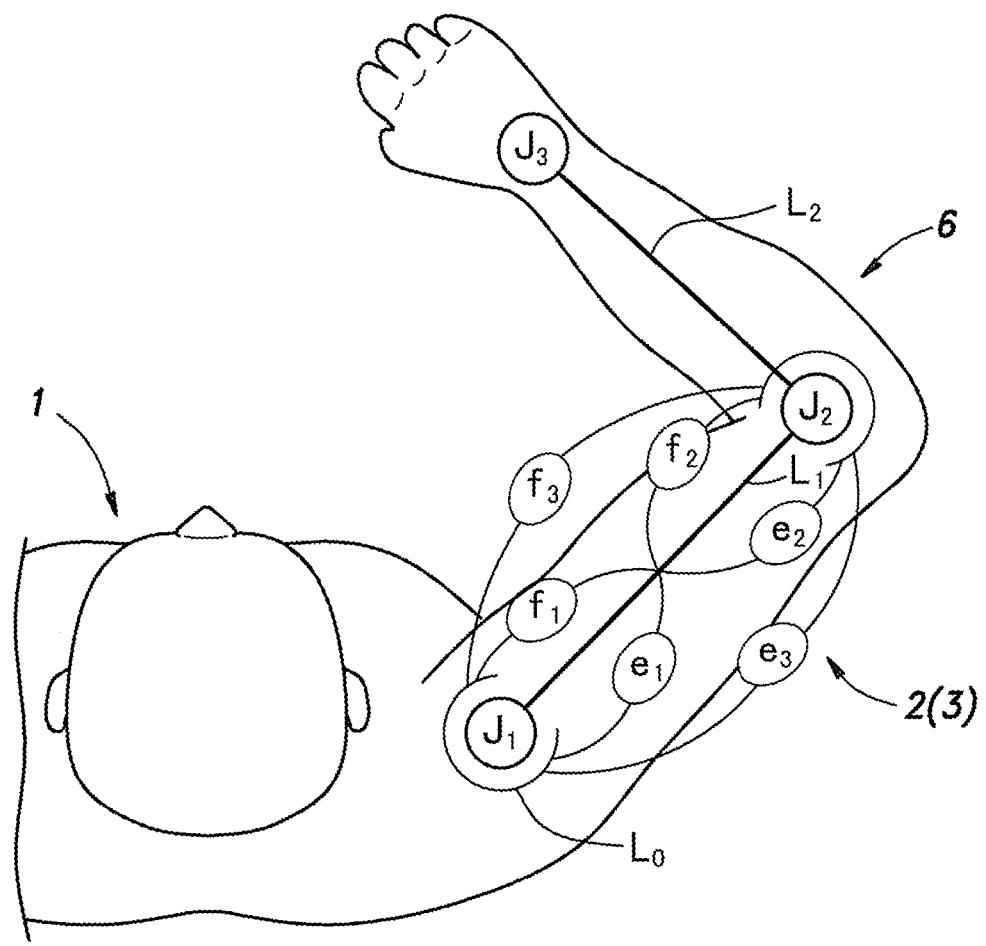
FIG. 1 is an explanatory view of a 3-pair of 6-muscle model for an upper limb.

In the 3-pair of 6-muscle model, as shown in FIG. 1, a limb 3 such as an upper limb 2 or a lower limb of a subject 1 is modeled as a two-joint link mechanism 6 having a first rod $L_1$ having a proximal end pivotally supported (supported) on a base body $L_0$ by a first joint $J_1$ and a second rod $L_2$ pivotally supported (supported) on a free end of the first rod $L_1$ by a second joint $J_2$. More specifically, when the upper limb is modeled, the base body $L_0$ corresponds to the scapula, the first joint $J_1$ corresponds to the shoulder joint, the first rod $L_1$ corresponds to the humerus, the second joint $J_2$ corresponds to the elbow joint, and the second rod $L_2$ corresponds to at least one of the radius and the ulna. Further, a free end $J_3$ of the second rod $L_2$ corresponds to the carpal joint portion. Hereinafter, the free end $J_3$ of the second rod $L_2$ will be referred to as a limb tip $J_3$.

The 3-pair of 6-muscle model which models muscles contributing to movement in a two-dimensional plane including the first joint $J_1$, the second joint $J_2$ and the limb tip $J_3$ of the limb 3 includes a first pair of antagonistic one-joint muscles $f_1$ and $e_1$ which straddle the first joint $J_1$, a second pair of antagonistic one-joint muscles $f_2$ and $e_2$ which straddle the second joint $J_2$, and a pair of antagonistic two-joint muscles $f_3$ and $e_3$ which straddle both the joints $J_1$ and $J_2$.

The first pair of antagonistic one-joint muscles f1 and e1 includes a muscle f1 which bends the first joint J1 and a muscle e1 which stretches the first joint J1. One end of each of the muscles f1 and e1 of the first pair of antagonistic one-joint muscles is attached to the base body L0, the other ends thereof are attached to the first rod L1, and the muscles f1 and e1 are provided to straddle the first joint J1. The first antagonistic one-joint muscle f1 corresponds to, for example, a front portion of the deltoid muscle, and the first antagonistic one-joint muscle e1 corresponds to, for example, a rear portion of the deltoid muscle.

The second pair of antagonistic one-joint muscles f2 and e2 includes a muscle f2 which bends the second joint J2 and a muscle e2 which stretches the second joint J2. One end of each of the muscles f2 and e2 of the second pair of antagonistic one-joint muscles is attached to the first rod L1, the other ends thereof are attached to the second rod L2, and the muscles f2 and e2 are provided to straddle the second joint J2. The second antagonistic one-joint muscle f2 corresponds to, for example, the brachial muscle, and the second antagonistic one-joint muscle e2 corresponds to, for example, an outer head of the triceps brachii muscle.

The pair of antagonistic two-joint muscles f3 and e3 includes a muscle f3 which simultaneously bends the first joint J1 and the second joint J2 and a muscle e3 which simultaneously stretches the first joint J1 and the second joint J2. One end of each of the pair of antagonistic two-joint muscles f3 and e3 is attached to the base body L0, the other ends thereof are attached to the second rod L2, and the pair of antagonistic two-joint muscles f3 and e3 are provided to straddle the first joint J1 and the second joint J2. The antagonistic two-joint muscle f3 corresponds to, for example, the biceps brachii muscle, and the antagonistic two-joint muscle e3 corresponds to, for example, an elongated head of the triceps brachii muscle.

Figure 2:
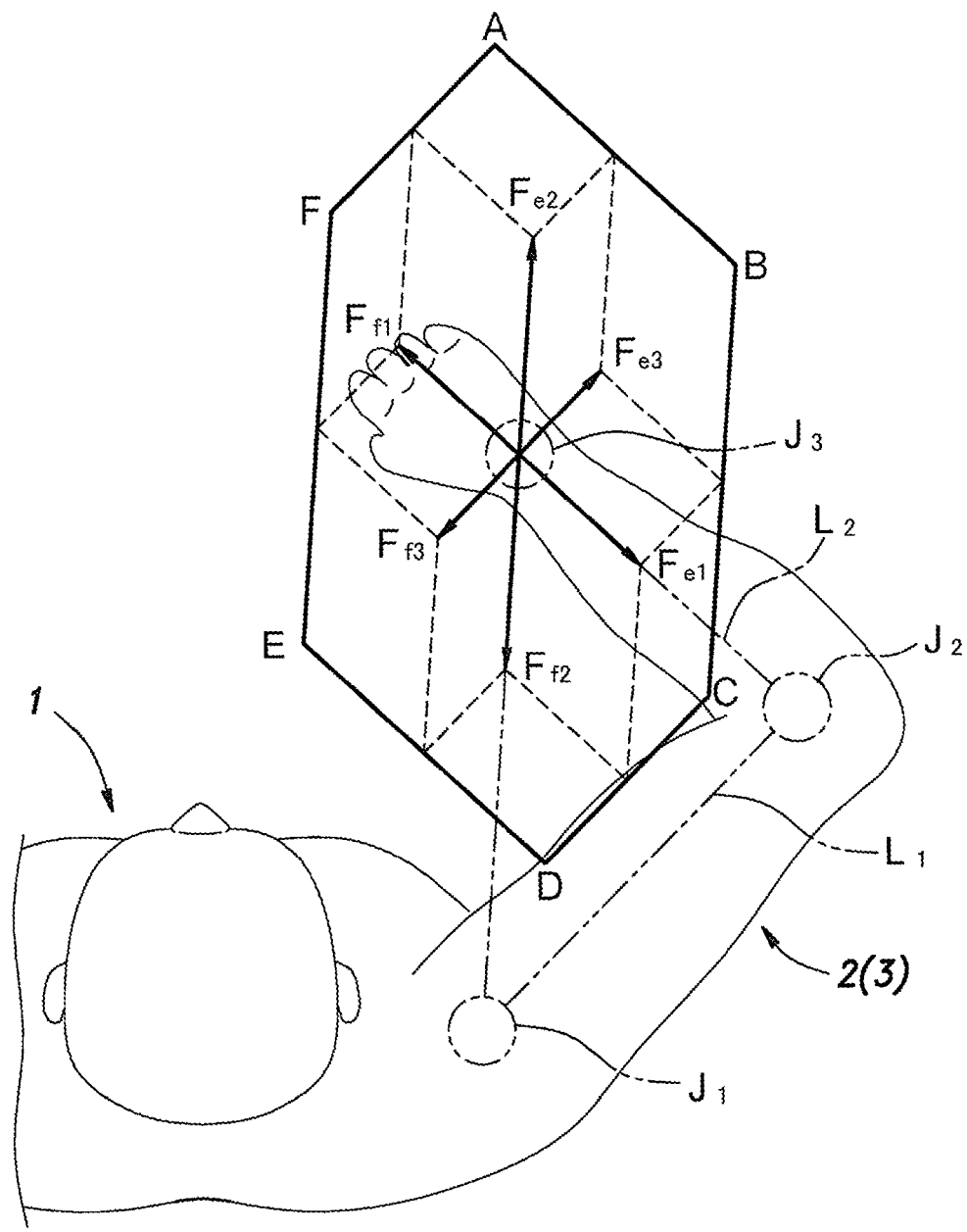
FIG. 2 is an explanatory view of a maximum output distribution at a tip of the upper limb.

A magnitude and direction of the output at the limb tip $J_3$ are determined by a combination of the outputs of the first pair of antagonistic one-joint muscles $f_1$ and $e_1$, the second pair of antagonistic one-joint muscles $f_2$ and $e_2$, and the pair of antagonistic two-joint muscles $f_3$ and $e_3$. Assuming that a maximum output which the first antagonistic one-joint muscle $f_1$ outputs to the limb tip $J_3$ is $F_{f1}$, a maximum output which the first antagonistic one-joint muscle $e_1$ outputs to the limb tip $J_3$ is $F_{e1}$, a maximum output which the second antagonistic one-joint muscle $f_2$ outputs to the limb tip $J_3$ is $F_{f2}$, a maximum output which the second antagonistic one-joint muscle $e_2$ outputs to the limb tip $J_3$ is $F_{e2}$, a maximum output which the antagonistic two-joint muscle $f_3$ outputs to the limb tip $J_3$ is $F_{f3}$, and a maximum output which the antagonistic two-joint muscle $e_3$ outputs to the limb tip $J_3$ is $F_{e3}$, a distribution diagram (hereinafter, maximum output distribution) of the maximum output obtained at the limb tip $J_3$ by these 3 pairs of 6 muscles is simply represented by a hexagon ABCDEF corresponding to the contribution of each muscle, as shown in FIG. 2. However, the maximum output (hereinafter, functional effective muscle strength) of each muscle is the largest force that each muscle can exert (output) and is represented by a vector in a plane defined by the first rod $L_1$ and the second rod $L_2$. Details of a method of calculating the hexagon ABCDEF are not described here because they are known, but for example, reference may be made to Non-Patent Document 1 described above.

In the hexagon ABCDEF, a side AB, a side DE, and the second rod $L_2$ are parallel to each other, and a side CD, a side FA, and the first rod $L_1$ are parallel to each other. Further, a side BC, a side EF, and a straight line which connects the limb tip $J_3$ to the first joint $J_1$ are parallel to each other. In FIG. 2, an output $F_A$ at a point A, an output $F_B$ at a point B, an output $F_C$ at a point C, an output $F_D$ at a point D, an output $F_E$ at a point E, and an output $F_F$ at a point F are expressed by Equation (1). The functional effective muscle strengths $F_{f1}$, $F_{f2}$, $F_{f3}$, $F_{e1}$, $F_{e2}$ and $F_{e3}$ of muscles can be calculated from the hexagon ABCDEF using Equation (1).

$$\begin{cases} F_A = F_{f1} + F_{e2} + F_{e3} \\ F_B = F_{e1} + F_{e2} + F_{e3} \\ F_C = F_{e1} + F_{f2} + F_{e3} \\ F_D = F_{e1} + F_{f2} + F_{f3} \\ F_E = F_{f1} + F_{f2} + F_{f3} \\ F_F = F_{f1} + F_{e2} + F_{f3} \end{cases} \quad (1)$$

Figure 3:
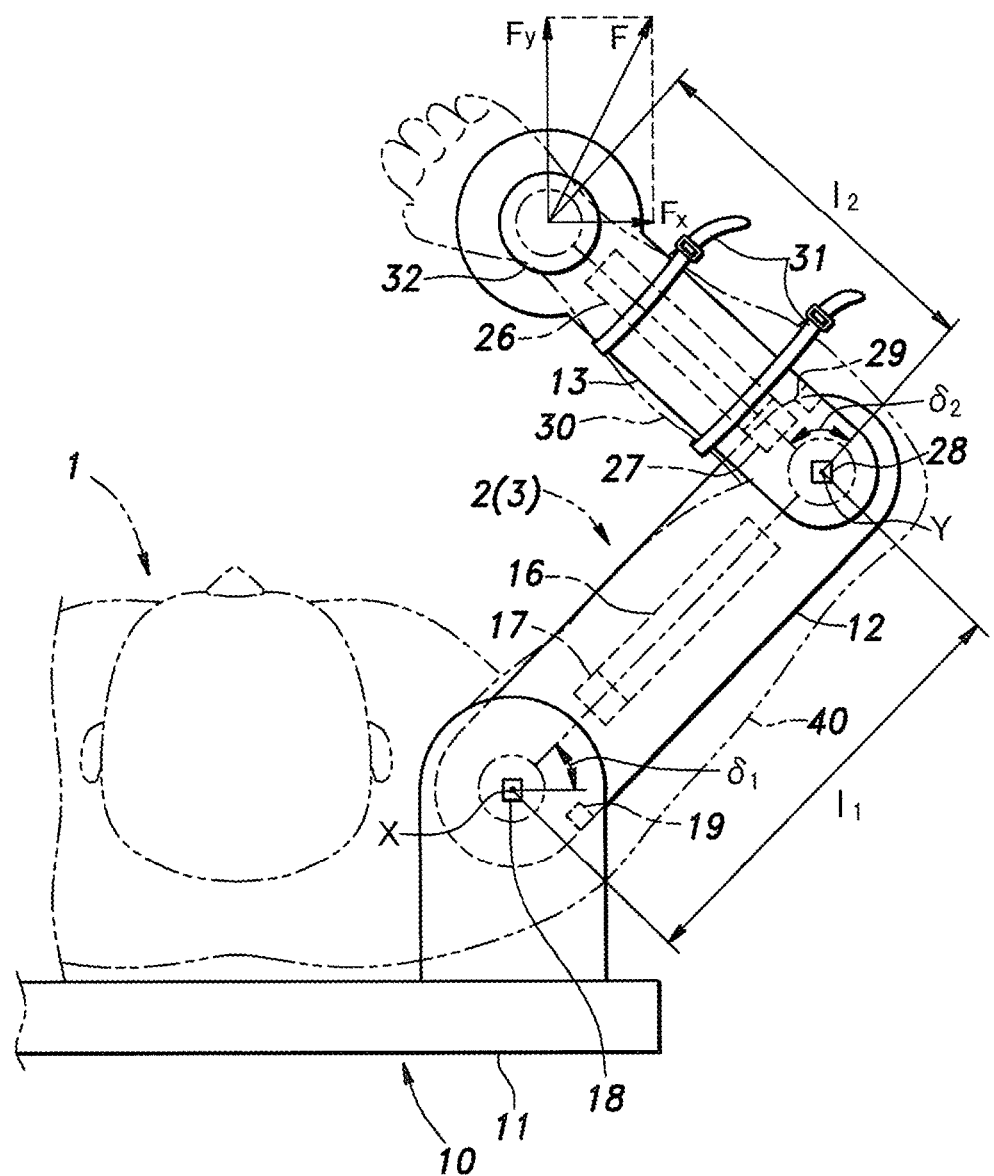
FIG. 3 is an explanatory view of a measuring device.

Next, a measuring device 10 for implementing the method for evaluating muscle strength characteristics according to the first embodiment will be described with reference to FIG. 3. The measuring device 10 includes a seat, a backrest 11 coupled to a rear of the seat, and a first link 12 of which one end is coupled to the backrest 11, a second link 13 coupled to the other end of the first link 12, and an arithmetic device 14 (refer to FIG. 4).

The first link 12 is a bar-like member which is substantially horizontal and extends in one direction. One end side of the first link 12 in an extension direction is coupled to the backrest 11 so that the first link 12 is pivotable about an axis X extending in a vertical direction. A first actuator 16 which changes a length of the first link 12 in the extension direction and a first control device 17 which controls driving of the first actuator 16 are provided at the first link 12. A first angle sensor 18 which measures a rotation angle of the first link 12 with respect to the backrest 11 and a known first locking mechanism 19 which locks the first link 12 so that it does not rotate with respect to the backrest 11 are provided between the first link 12 and the backrest 11.

The second link 13 is a bar-like member which is substantially horizontal and extends in one direction. One end side of the second link 13 in an extension direction is coupled to the other end side of the first link 12 in the extension direction so that the second link 13 is pivotable about an axis Y extending in the vertical direction. A second actuator 26 which changes a length of the second link 13 in the extension direction and a second control device 27 which controls driving of the second actuator 26 are provided at the second link 13. A second angle sensor 28 which measures a rotation angle of the second link 13 with respect to the first link 12 and a known second locking mechanism 29 which locks the second link 13 so that it does not rotate with respect to the first link 12 are provided between the first link 12 and the second link 13. A plurality of belts 31 (fixing tools) for fixing a forearm 30 of the subject 1 are provided on the second link 13 at intervals in the extension direction thereof.

A force sensor 32 is provided on the other end side of the second link 13, that is, on the free end side of the second link 13. The force sensor 32 is a known sensor which detects an in-plane force applied to an upper surface of the force sensor and is disposed in a manner that the upper surface of the force sensor 32 is flush with an upper surface of the second link 13 and is substantially horizontal. The force sensor 32 may be, for example, a capacitive sensor. In this embodiment, as shown in FIG. 3, the force sensor 32 divides a vector F of a force applied to the upper surface of the force sensor 32 into a component Fx of the force in an x-axis direction which is substantially parallel to the backrest 11 and faces the right side of the subject 1 and a component Fy of the force in a y-axis direction which is perpendicular to the x axis and faces a front of the subject 1 and then outputs them. The vector F of the force measured by the force sensor 32 corresponds to one point (Fx, Fy) on xy coordinates defined in a substantially horizontal plane with the upper surface of the force sensor 32 as an origin O.

Figure 4:
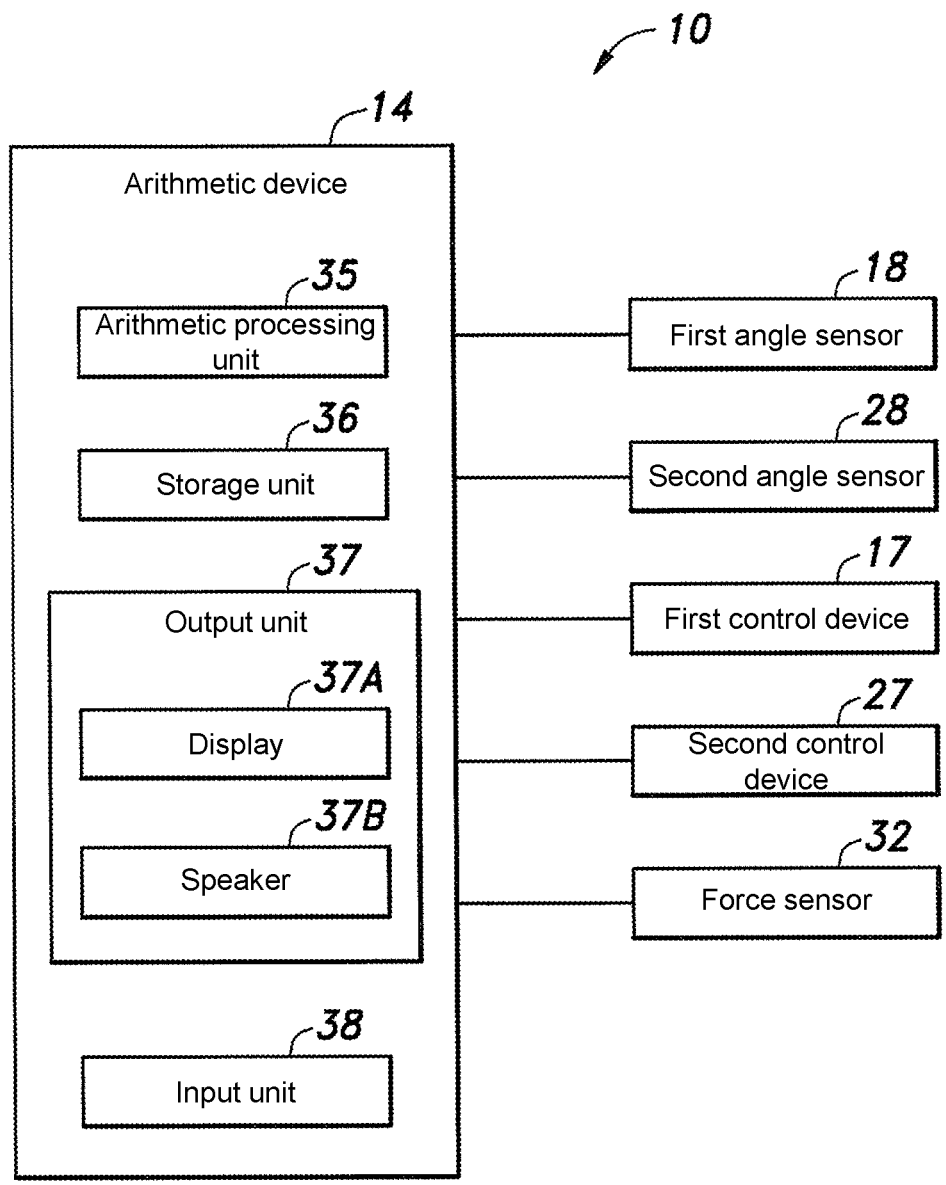
FIG. 4 is a block diagram of the measuring device.

As shown in FIG. 4, the arithmetic device 14 is a computer including an arithmetic processing unit 35 such as a central processing unit (CPU) which performs arithmetic processing, a storage unit 36 such as a memory and a hard disk which holds information, an output unit 37 such as a display 37A and a speaker 37B, and an input unit 38. The arithmetic device 14 is connected to the first angle sensor 18, the second angle sensor 28, the first control device 17, the second control device 27, and the force sensor 32 through a predetermined cable at the input unit 38.

When the muscle strength of the upper limb 2 of the subject 1 is evaluated, after the subject 1 sits on the seat, his/her back is placed along the backrest 11, and his/her torso is fixed to the backrest 11 by a belt or the like. Therefore, since the subject's torso does not move, the muscle strength characteristics can be evaluated more appropriately. Thereafter, the subject 1 places an upper arm 40 along the upper surface of the first link 12 and places the forearm 30 along the upper surface of the second link 13. At this time, the subject 1 drives the first actuator 16 and the second actuator 26 so that the shoulder joint (the first joint) $J_1$ is aligned with the axis X, the elbow joint (the second joint) $J_2$ is aligned with the axis Y and the carpal joint (the limb tip) $J_3$ is in contact with the upper surface of the force sensor 32, and thus the length of each of the first link 12 and the second link 13 may be adjusted. Next, the subject 1 fixes the forearm 30 to the second link 13 using the belt 31 and locks the links 12 and 13 such that they do not rotate using the locking mechanisms 19 and 29. Thereafter, the arithmetic device 14 performs the muscle strength evaluation processing.

Figure 8:
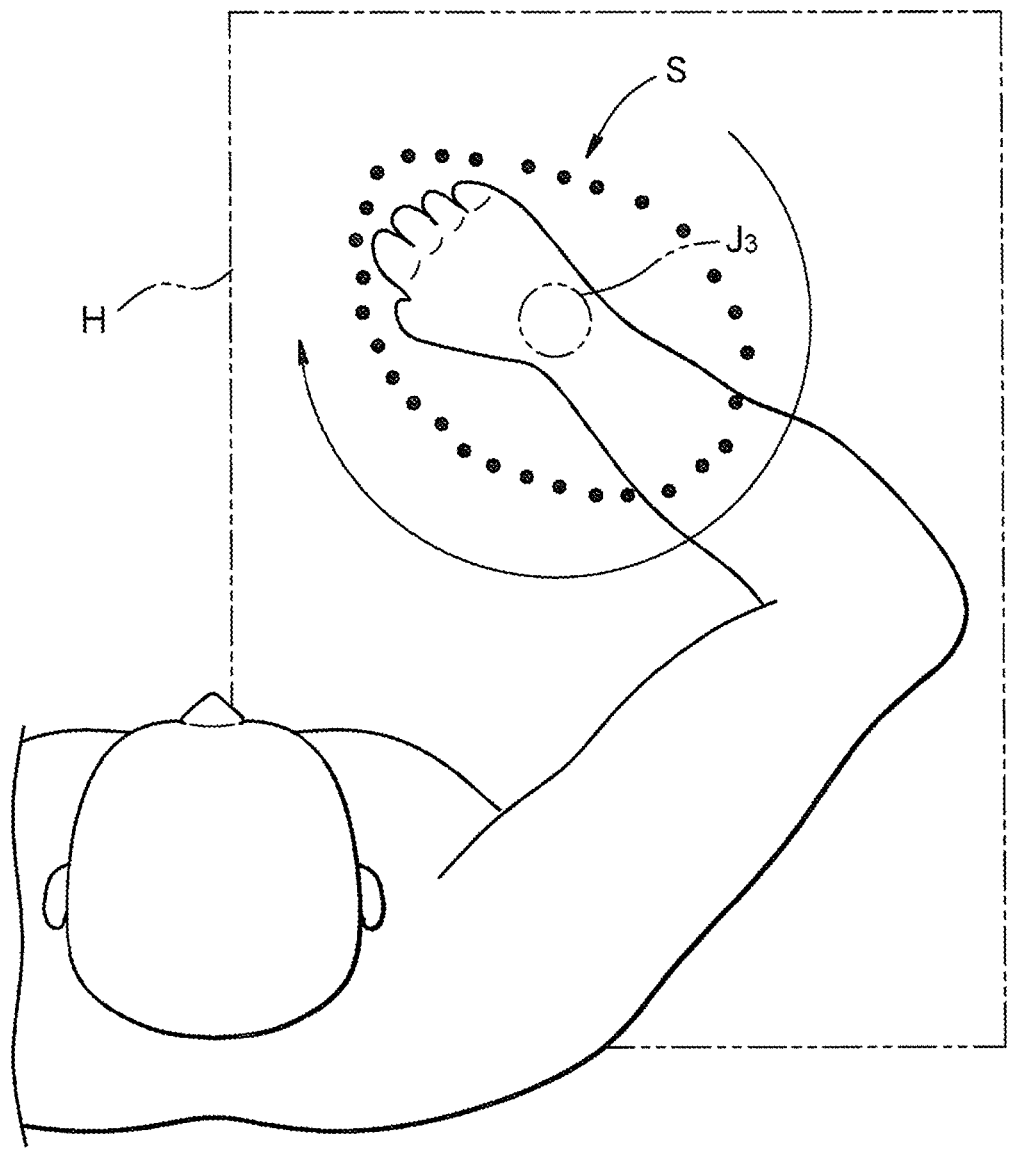
FIG. 8 is a diagram showing measurement results of an orbiting output.

While the muscle strength evaluation processing is performed, the humerus (the first rod) $L_1$, and the radius and ulna (the second rod) $L_2$ of the subject 1 are disposed along a substantially horizontal measurement surface H (refer to FIG. 8). Further, the shoulder joint $J_1$ (the first joint) of the subject 1 and the elbow joint $J_2$ (the second joint) are held at a predetermined angle by the locking of the locking mechanisms 19 and 29 and the belt 31, and a posture of the subject 1 is kept constant. Also, before the muscle strength evaluation processing is performed, the arithmetic device 14 may instruct the subject 1 to turn his/her palm downward using sound generated from the speaker 37B.

In the muscle strength evaluation processing, the arithmetic device 14 may receive a signal from the first angle sensor 18 at the input unit 38 and may calculate an angle $\theta_1$ (refer to FIG. 3) of the first joint $J_1$ (the shoulder joint) of the subject 1 based on the received signal. Further, the arithmetic device 14 may receive a signal from the second angle sensor 28 at the input unit 38 and may calculate an angle $\delta_2$ (refer to FIG. 3) of the second joint $J_2$ (the elbow joint) of the subject 1 based on the received signal. The arithmetic device 14 may receive a signal from the first control device 17 at the input unit 38 and may calculate a length $l_1$ (refer to FIG. 3) of the upper arm 40 of the subject 1, that is, the first rod $L_1$ based on the received signal. The arithmetic device 14 may receive a signal from the second control device 27 at the input unit 38 and may calculate a length $l_2$ (refer to FIG. 3) of the forearm 30 of the subject 1, that is, the second rod $L_2$ based on the received signal.

Figure 5:
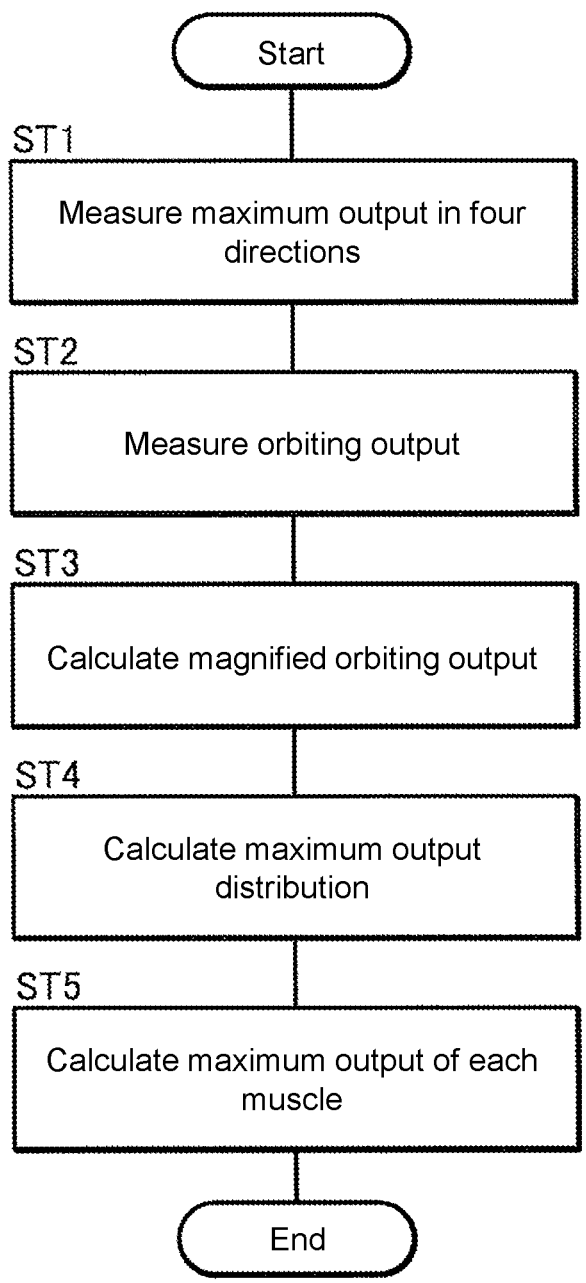
FIG. 5 is a flowchart of muscle strength evaluation processing.

Next, the muscle strength evaluation processing performed in the arithmetic device 14 will be described with reference to FIG. 5.

In initial Step ST1 of the muscle strength evaluation processing, the arithmetic device 14 measures the maximum output in four directions by instructing the subject 1 to exert the maximum output in the four directions. The measurement of the maximum output in the four directions may be similar to the four-point measurement method described in Patent Document 1. Specifically, first, the arithmetic device 14 instructs the subject 1 to exert as much force as possible in a direction (hereinafter, a first direction) in which the second joint $J_2$ is stretched to the limb tip $J_3$ within a predetermined measurement time. The first direction is defined in a plane defined by the upper arm 40 (the first rod $L_1$) and the forearm 30 (the second rod $L_2$), that is, in a measurement plane H and is generally a forward direction with respect to the subject 1. The instruction to the subject 1 may be performed using display on the display 37A or sound from the speaker 37B. The force exerted by the subject 1 on the limb tip $J_3$ is applied to the upper surface of the force sensor 32. The arithmetic device 14 extracts and stores a vector $F_1$ of the largest force applied to the upper surface of the force sensor 32 within the measurement time based on the output from the force sensor 32. Next, the subject 1 is instructed to exert a force as much as possible in a direction in which the second joint $J_2$ bends at the limb tip $J_3$, that is, in a direction opposite to the first direction within a predetermined measurement time. The arithmetic device 14 extracts and stores a vector $F_3$ of the largest force applied to the upper surface of the force sensor 32 within the measurement time.

Figure 7:
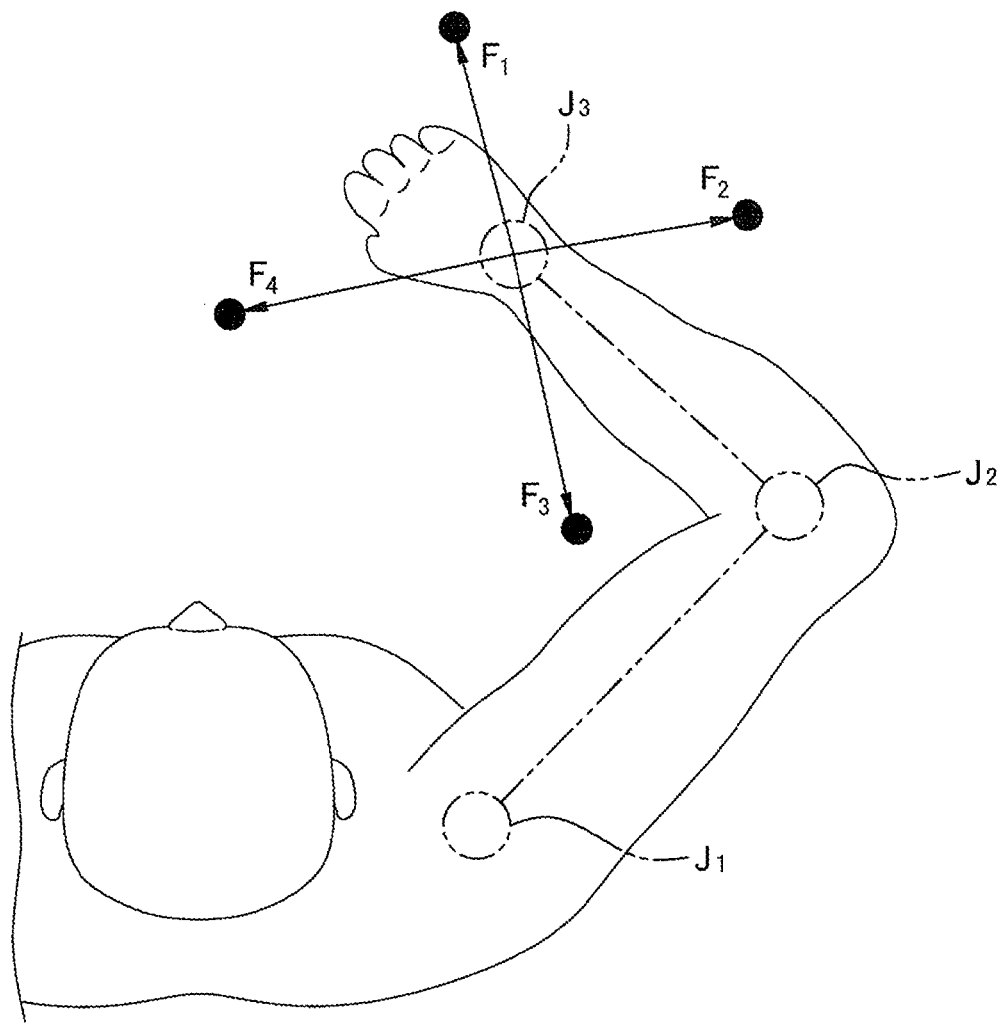
FIG. 7 is a diagram showing measurement results of four maximum outputs obtained by a four-point measurement method.

Next, the arithmetic device 14 calculates a second direction which is parallel to the measurement plane H and is orthogonal to that of a difference ($F_1-F_3$) between $F_1$ and $F_3$ and in which both the first joint $J_1$ and the second joint $J_2$ are stretched. Furthermore, the arithmetic device 14 instructs the subject 1 to exert as much force as possible in the second direction on the limb tip $J_3$ within a predetermined measurement time. The arithmetic device 14 extracts and stores a vector $F_2$ of the largest force applied to the upper surface of the force sensor 32 within the measurement time based on an output from the force sensor 32. Next, the arithmetic device 14 instructs the subject 1 to exert as much force as possible in a direction opposite to the second direction on the limb tip $J_3$ within a predetermined measurement time. The arithmetic device 14 extracts and stores a vector $F_4$ of the largest force applied to the upper surface of the force sensor 32 within the measurement time based on an output from the force sensor 32, and thus Step ST1 is completed. As shown in FIG. 7, the four vectors $F_1$, $F_2$, $F_3$ and $F_4$ of force respectively correspond to four points in the xy coordinates.

When Step ST1 is completed, the arithmetic device 14 performs Step ST2. In Step ST2, the arithmetic device 14 measures an orbiting output S of the limb tip $J_3$ in all directions in the measurement plane H. More specifically, the arithmetic device 14 instructs the subject 1 to exert a force in a circumferential direction, that is, while changing the direction through 360 degrees, along the upper surface of the force sensor 32, that is, within the measurement plane H from the limb tip $J_3$ over a predetermined measurement time (for example, 5 seconds to 10 seconds). In the embodiment, the arithmetic device 14 instructs the subject 1 to exert a force while changing the direction in a clockwise direction (a direction of an arrow in FIG. 8) in a top view. At this time, the arithmetic device 14 does not need to instruct the subject 1 to exert as much force as possible on the upper surface of the force sensor 32. The arithmetic device 14 obtains a vector of force applied to the upper surface of force sensor 32 at predetermined timings within the measurement time based on the output from force sensor 32. Furthermore, the arithmetic device 14 stores a group of the vectors of force acquired within the measurement time as the orbiting output S, and thus Step ST2 is completed. The orbiting output S corresponds to a group of points (refer to FIG. 8) arranged approximately in the form of a ring in the xy coordinates.

When Step ST2 is completed, the arithmetic device 14 performs Step ST3. In Step ST3, the arithmetic device 14 calculates a half straight line $OF_1$, a half straight line $OF_2$, a half straight line $OF_3$ and a half straight line $OF_4$ extending outward through each point with the origin O as a starting point with respect to each point of the maximum outputs $F_1$, $F_2$, $F_3$ and $F_4$. Next, for each point of the maximum outputs $F_1$, $F_2$, $F_3$ and $F_4$, the arithmetic device 14 extracts a point closest to the corresponding half straight line from the orbiting output S. Thereafter, the arithmetic device 14 calculates ratios $\alpha_1$, $\alpha_2$, $\alpha_3$ and $\alpha_4$ of a distance between the extracted point and the origin O to a magnitude of the corresponding maximum output. For example, when the point closest to the half straight line $OF_1$ with respect to the maximum output $F_1$ is $F_1'$, $\alpha_1$ is expressed as $\alpha_1 = |F_1|/|F_1'|$. Here, $|x|$ represents a distance from the origin O (that is, the magnitude of the vector of force).

Next, angles $\theta_1$, $\theta_2$, $\theta_3$ and $\theta_4$ with respect to the x axis are calculated for the maximum outputs $F_1$, $F_2$, $F_3$ and $F_4$, respectively. For each point $F_S$ of the orbiting output S, an angle $\theta$ between the x-axis and a straight line connecting the point with the origin O is calculated, and a magnification factor k for each of vectors $F_S$ of force included in the orbiting output S is calculated based on the following Equation (2).

$$\begin{cases} k = \frac{\alpha_1 - \alpha_2}{\theta_1 - \theta_2} \cdot (\theta - \theta_2) + \alpha_2 & (\theta_2 \leq \theta < \theta_1) \\ k = \frac{\alpha_2 - \alpha_3}{\theta_2 - \theta_3} \cdot (\theta - \theta_3) + \alpha_3 & (\theta_3 \leq \theta < \theta_2) \\ k = \frac{\alpha_3 - \alpha_4}{\theta_3 - \theta_4} \cdot (\theta - \theta_4) + \alpha_4 & (\theta_4 \leq \theta < \theta_3) \\ k = \frac{\alpha_4 - \alpha_1}{\theta_4 - \theta_1} \cdot (\theta - \theta_1) + \alpha_1 & (\theta_1 \leq \theta < \theta_4) \end{cases} \quad (2)$$

Figure 9A:
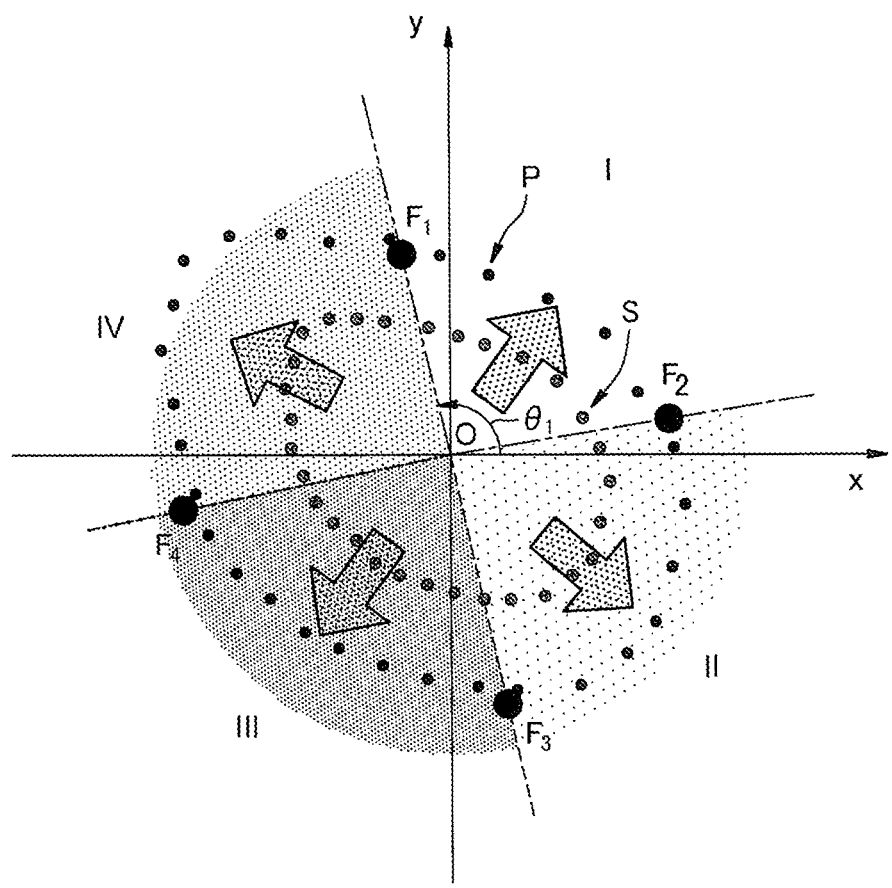
FIG. 9A is an explanatory diagram for explaining a method for calculating a magnified orbiting output.
Figure 9B:
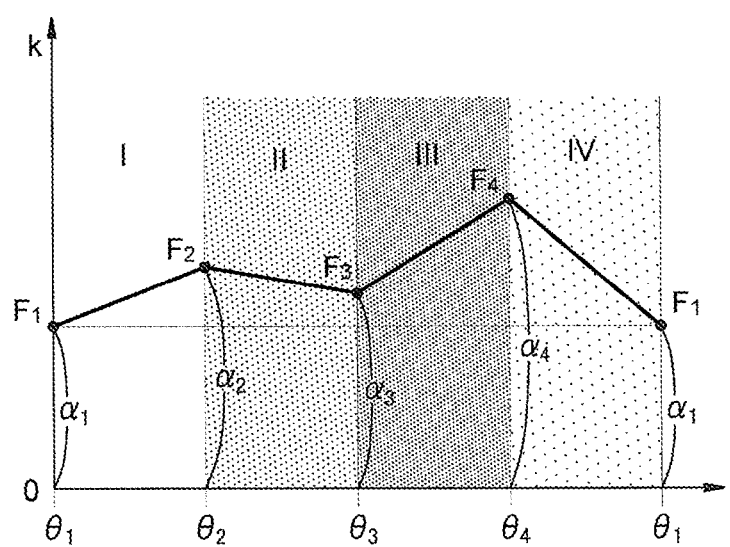
FIG. 9B is a graph showing direction dependence of a magnification factor

The magnification factor k is represented by a linear function of the angle $\theta$ shown in Equation (2) in each of a region I sandwiched by the half straight line $OF_1$ and the half straight line $OF_2$, a region II sandwiched by the half straight line $OF_2$ and the half straight line $OF_3$, a region III sandwiched by the half straight line $OF_3$ and the half straight line $OF_4$ and a region IV sandwiched by the half straight line $OF_4$ and the half straight line $OF_1$ shown in FIG. 9A. Also, the relationship between k and $\theta$ is shown in FIG. 9B. The magnification factor k corresponds to that linearly interpolated for the angle $\theta$ with respect to the x axis using the magnification factors $\alpha_1$, $\alpha_2$, $\alpha_3$ and $\alpha_4$ at boundaries in the regions I, II, III and IV.

Next, the arithmetic device 14 performs magnification correction on the orbiting output S and calculates a magnified orbiting output P (refer to FIG. 9A) by multiplying each of the vectors of force included in the orbiting output S by the corresponding magnification factor k. The arithmetic device 14 stores the calculated magnified orbiting output P, and thus Step ST3 is completed.

Figure 6:
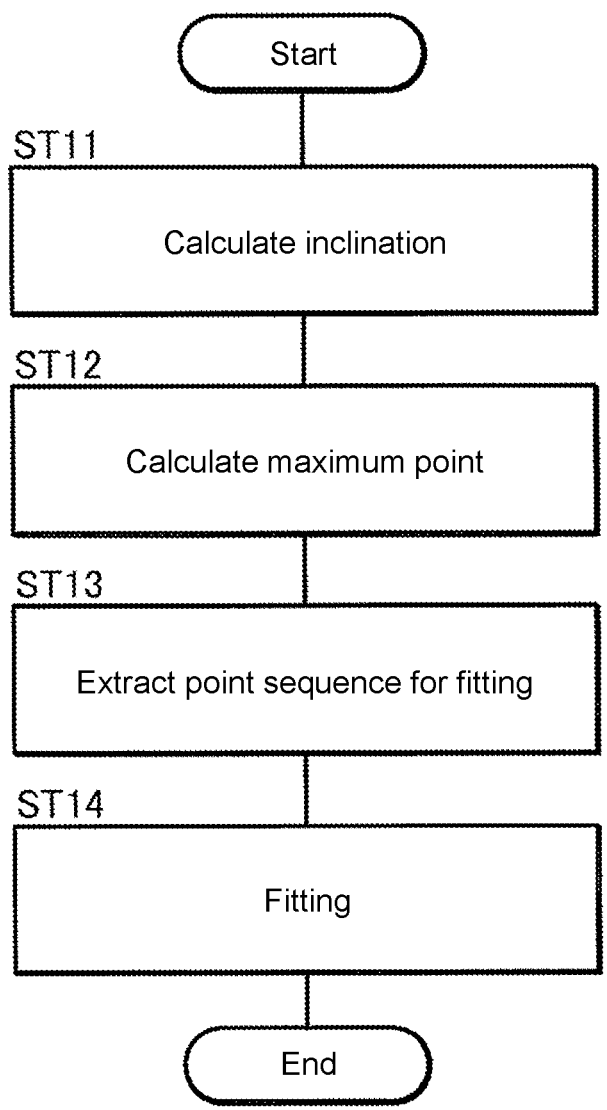
FIG. 6 is a flowchart of approximation processing.

When Step ST3 is completed, the arithmetic device 14 performs Step ST4. In Step ST4, the arithmetic device 14 creates a hexagon corresponding to the maximum output distribution Q from the magnified orbiting output P. More specifically, the arithmetic device 14 performs approximation processing which calculates an approximate straight line for six sides forming the hexagon based on the magnified orbiting output P. Hereinafter, the details of the approximation processing will be described below with reference to FIG. 6.

Figure 10A:
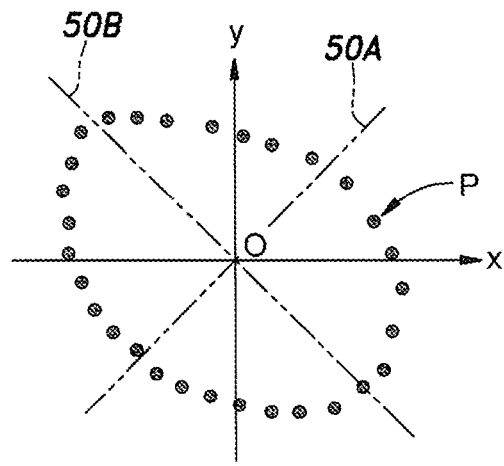
FIGS. 10A-10D are explanatory diagrams for explaining processing in the approximation processing.

In initial Step ST11 of the approximation processing, first, the arithmetic device 14 calculates the angle $\delta_1$ of the first joint $J_1$ (the shoulder joint) based on the output of the first angle sensor 18 and calculates the angle $\delta_2$ of the second joint $J_2$ (the elbow joint) based on the output of the second angle sensor 28. Next, the arithmetic device 14 calculates the length $l_1$ of the forearm 30 (the first rod $L_1$) based on the output of the first control device 17 and calculates the length $l_2$ of the upper arm 40 (the second rod $L_2$) based on the output of the second control device 27. Thereafter, the arithmetic device 14 calculates a theoretical inclination of the side corresponding to the approximate straight line to be derived based on $\delta_1$, $\delta_2$, $l_1$ and $l_2$. As shown in FIG. 2, the inclination of the side corresponding to the approximate straight line to be derived may be calculated using the facts that the side AB is parallel to the second rod $L_2$, the side CD is parallel to the first rod $L_1$, and the side BC is parallel to a straight line connecting the limb tip $J_3$ with the first joint $J_1$. In FIG. 10A, as an example, a straight line 50A having a theoretical inclination calculated with respect to the side AF and passing through the origin O is illustrated.

When Step ST11 is completed, the arithmetic device 14 performs Step ST12. In Step ST12, first, the arithmetic device 14 obtains a straight line 50B which is orthogonal to the straight line 50A having the inclination calculated in Step ST11 and passes through the origin O (FIG. 10(A)).

Figure 10B:
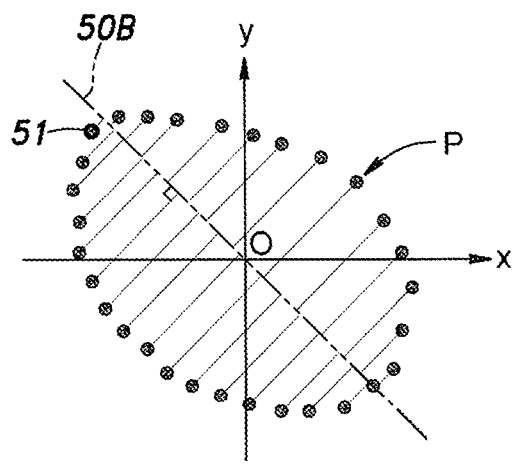

Next, an intersection point is obtained by drawing a vertical line from each point included in the magnified orbiting output P to the obtained straight line 50B. Among the obtained intersection points, a point located farthest from the origin O and located on the side (the side AB) corresponding to the approximate straight line to be derived is extracted as the maximum point 51 (FIG. 10B). The arithmetic device 14 stores the extracted maximum point 51, and thus Step ST12 is completed.

Figure 10C:
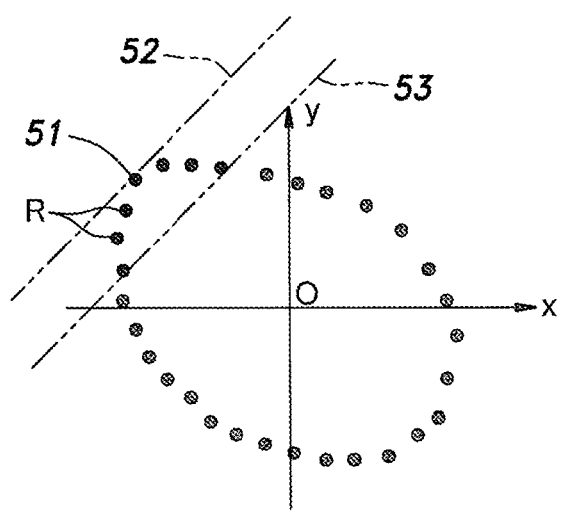

When Step ST12 is completed, the arithmetic device 14 performs Step ST13. In Step ST13, the arithmetic device 14 calculates a first virtual line 52 which passes through the maximum point 51 and has the theoretical inclination calculated in Step ST11, and a second virtual line 53 which is parallel to the first virtual line 52 and is located on the side of the origin O by a predetermined value (for example, 50 N) in a direction orthogonal to the first virtual line 52 (FIG. 10C). Next, the arithmetic device 14 extracts and stores a point located between the first virtual line 52 and the second virtual line 53 in the magnified orbiting output P as point sequence R for fitting, and thus Step ST13 is completed.

Figure 10D:
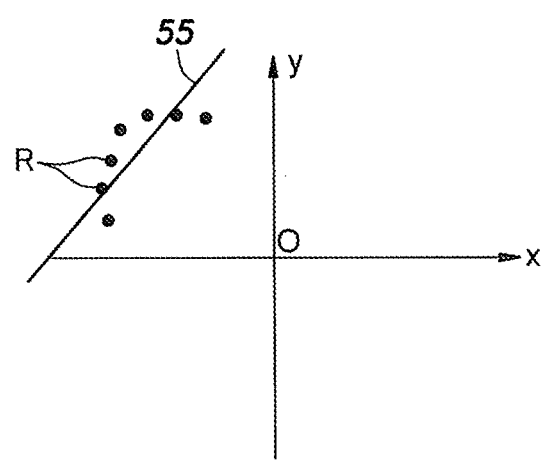

When Step ST13 is completed, the arithmetic device 14 performs Step ST14. In Step ST14, the arithmetic device 14 calculates an approximate straight line 55 by fitting the point sequence R for fitting with a straight line (FIG. 10D), and thus the approximation processing is completed.

Figure 11:
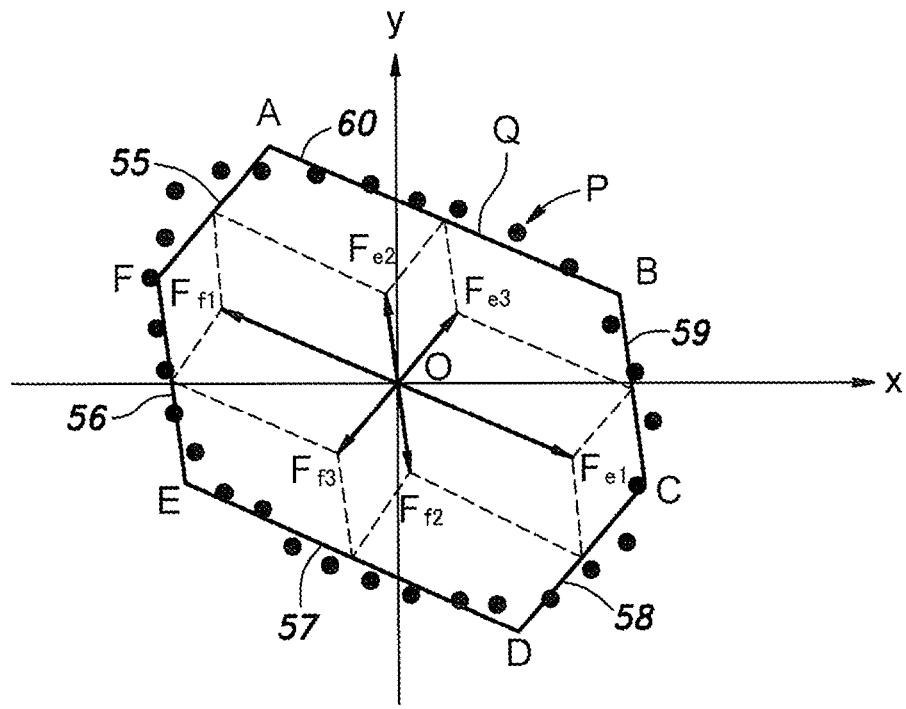
FIG. 11 is a diagram showing a calculated maximum output distribution and a calculated functional effective muscle strength of each muscle.

The arithmetic device 14 calculates six approximate straight lines 55 to 60 by performing the approximation processing on each of the six sides forming the hexagon. Therefore, as shown in FIG. 11, the arithmetic device 14 acquires a hexagonal maximum output distribution Q (Step ST4). After the maximum output distribution Q is acquired, in Step ST5, the arithmetic device 14 calculates functional effective muscle strengths $F_{f1}$, $F_{f2}$, $F_{f3}$, $F_{e1}$, $F_{e2}$ and $F_{e3}$ of muscles from the maximum output distribution Q based on Equation (1). Further, the arithmetic device 14 may calculate the functional effective muscle strengths $F_{f1}$, $F_{f2}$, $F_{f3}$, $F_{e1}$, $F_{e2}$ and $F_{e3}$ of muscles by setting an appropriate numerical value to a ratio of the magnitudes of two antagonistic muscle strengths, for example, $|F_{f1}|/(|F_{f1}|+|F_{e1}|)$ or the like, in addition to the hexagon ABCDEF and Equation (1). Next, the arithmetic device 14 displays magnitudes of the calculated functional effective muscle strengths $|F_{f1}|$, $|F_{f2}|$, $|F_{f3}|$, $|F_{e1}|$, $|F_{e2}|$ and $|F_{e3}|$ of muscles on the display 37A, and thus the muscle strength evaluation processing is finished.

Next, effects of the method for evaluating muscle strength characteristics configured as described above will be described. The four-point measurement method in which the functional effective muscle strength of each muscle is calculated based on the four maximum outputs $F_1$, $F_2$, $F_3$ and $F_4$ and the method for evaluating muscle strength characteristics according to the embodiment of the disclosure were performed five times for the same subject 1, and the magnitude of the functional effective muscle strength of each muscle was calculated each time. Table 1 shows the magnitude of the functional effective muscle strength of each muscle calculated by the four-point measurement method at each time and the standard deviation of the magnitude of the functional effective muscle strength of each muscle obtained by five measurements. Table 2 shows the magnitude of the functional effective muscle strength of each muscle calculated by the method for evaluating muscle strength characteristics according to the embodiment of the disclosure at each time and the standard deviation of the magnitude of the functional effective muscle strength of each muscle obtained by five measurements.

TABLE 1

| [N] | first time | second time | third time | fourth time | fifth time | standard deviation |
|---|---|---|---|---|---|---|
| $e_1$ | 158.666 | 162.1456 | 113.7092 | 139.5818 | 174.1524 | 23.61623 |
| $e_2$ | 165.9481 | 145.3586 | 35.3795 | 124.1087 | 106.3884 | 50.03237 |
| $e_3$ | 78.2154 | 68.7963 | 132.5901 | 74.1489 | 75.5137 | 26.35103 |
| $f_1$ | 231.2595 | 233.1684 | 180.7295 | 230.9553 | 250.8183 | 26.30155 |
| $f_2$ | 170.3982 | 136.8986 | 140.8396 | 115.5387 | 105.0684 | 25.28612 |
| $f_3$ | 78.2154 | 68.7963 | 132.5901 | 74.1489 | 75.5137 | 26.35103 |

TABLE 2

| [N] | first time | second time | third time | fourth time | fifth time | standard deviation |
|---|---|---|---|---|---|---|
| $e_1$ | 134.1088 | 103.0438 | 123.2796 | 121.4134 | 137.5468 | 13.52776 |
| $e_2$ | 158.5452 | 221.3646 | 170.0726 | 133.4503 | 184.7406 | 32.62151 |
| $e_3$ | 85.2037 | 117.132 | 113.9932 | 78.4377 | 81.6816 | 18.69361 |
| $f_1$ | 257.5686 | 169.367 | 172.3587 | 229.6782 | 223.3397 | 38.38877 |
| $f_2$ | 201.8842 | 145.9553 | 101.6415 | 140.8392 | 150.271 | 35.75319 |
| $f_3$ | 85.2037 | 117.132 | 113.9932 | 78.4377 | 81.6816 | 18.69361 |

As shown in Table 1 and Table 2, the standard deviation obtained by the method for evaluating muscle strength characteristics according to the embodiment is smaller than the standard deviation obtained by the four-point measurement method in four muscles excluding $f_1$ and $f_2$. Moreover, when an average value of the standard deviation obtained by the four-point measurement method was calculated based on Table 1, the average value was 29.65. On the other hand, when an average value of the standard deviation obtained by the method for evaluating muscle strength characteristics according to the embodiment was calculated based on Table 2, the average value was 26.28. From these facts, it can be confirmed that variation in the measurement results obtained by the method for evaluating muscle strength characteristics according to the embodiment can be minimized as compared to the case obtained by the four-point measurement method. Thus, reproducibility and reliability of the maximum output distribution Q in the muscle strength evaluation method of the embodiment of the disclosure can be improved compared with in the four-point measurement method by adding the orbiting output S to the maximum outputs $F_1$ to $F_4$.

Further, in the embodiment, in Step ST1, the maximum outputs $F_1$ to $F_4$ are measured in two or more four different directions, and in Step ST3, the magnification factor k dependent on the direction is set for each point of the orbiting output S in accordance with the maximum outputs $F_1$ to $F_4$ corresponding to the different directions. The orbiting output S is magnified and corrected according to the magnification factor k, and the magnified orbiting output P is calculated. That is, since the orbiting output S is magnified and deformed to approach the plurality of measured maximum outputs $F_1$ to $F_4$, the obtained magnified orbiting output P approaches the actual maximum output distribution. Thus, the reproducibility and reliability of the maximum output distribution Q obtained based on the magnified orbiting output P can be enhanced.

In the embodiment, the functional effective muscle strengths $F_{f1}$, $F_{f2}$, $F_{f3}$, $F_{e1}$, $F_{e2}$ and $F_{e3}$ of the muscle group model, that is, the maximum output which is a contribution amount of each muscle is calculated based on the maximum output distribution Q. Therefore, a muscle group model close to the muscle strength characteristics of the subject 1 can be constructed. Accordingly, for example, it will be easier to identify the muscles to be reinforced in rehabilitation treatments. In addition, the muscle strength evaluation based on the muscle group model of each of a plurality of athletes can be performed by implementing the embodiment of the disclosure for the plurality of athletes. Thus, it is possible to carry out training based on the evaluation.

Second Embodiment

Next, a method for evaluating muscle strength characteristics according to a second embodiment will be described. The method for evaluating muscle strength characteristics according to a second embodiment is performed by a measurement device having the same configuration as that in the first embodiment, and the muscle strength evaluation processing performed by the measurement device is the same as that in the first embodiment except Step ST3. Therefore, the details of Step ST3 will be described below, and the other descriptions will be omitted.

Figure 12:
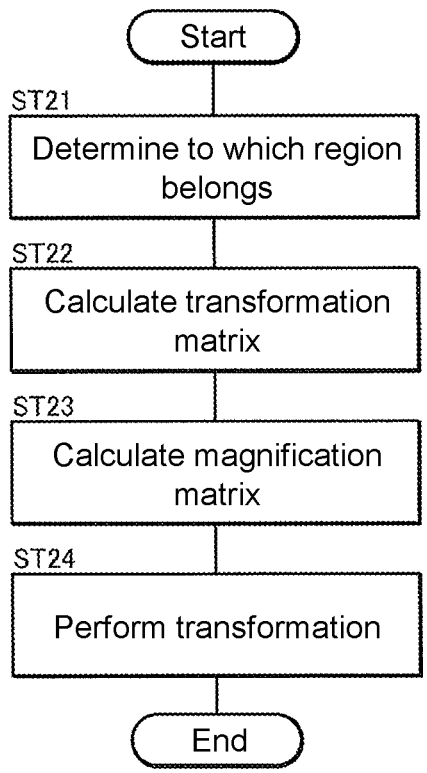
FIG. 12 is a flowchart of linear transformation processing in muscle strength evaluation processing according to a second embodiment.

In Step ST3, the arithmetic device 14 calculates $\alpha_1$, $\alpha_2$, $\alpha_3$, and $\alpha_4$ as in the first embodiment. Next, the arithmetic device 14 performs predetermined linear transformation processing on each of the vectors $F_S$ of force included in the orbiting output S, transforms them into $F_P$ and outputs a set of $F_P$ as the magnified orbiting output P. Hereinafter, the linear transformation processing will be described in detail with reference to FIG. 12.

In initial Step ST21 of the linear transformation processing, the arithmetic device 14 determines to which one of the regions I to IV shown in FIG. 9 $F_S$ belongs. In the following, the region to which $F_S$ belongs is described as a region r.

Next, in Step ST22, the arithmetic device 14 derives vectors $F_i$ and $F_j$ of force which define a boundary of the region r. More specifically, vectors of force which define the boundary of region I are $F_1$ and $F_2$, vectors of forces which define the boundary of region II are $F_2$ and $F_3$, vectors of forces which define the boundary of region III are $F_3$ and $F_4$, and vectors of forces which define the boundary of region IV are $F_4$ and $F_1$. After that, the arithmetic device 14 calculates the following transformation matrix T using an x component ($F_{ix}$) and a y component ($F_{iy}$) of the extracted vector $F_i$ of force and an x component ($F_{jx}$) and the y component ($F_{jy}$) of the extracted vector $F_j$ of force.

$$T = \begin{pmatrix} \dfrac{F_{ix}}{\sqrt{F_{ix}^2 + F_{iy}^2}} & \dfrac{F_{jx}}{\sqrt{F_{jx}^2 + F_{jy}^2}} \\ \dfrac{F_{iy}}{\sqrt{F_{ix}^2 + F_{iy}^2}} & \dfrac{F_{jy}}{\sqrt{F_{jx}^2 + F_{jy}^2}} \end{pmatrix} \quad (3)$$

The transformation matrix T is a matrix in which a vector of force represented on a coordinate system having a unit vector $e_i$ in a direction along the vector $F_i$ and a unit vector $e_j$ in a direction along the vector $F_j$ as basis vectors is transformed into a vector of force on an xy coordinate system. The first column of the transformation matrix represents $e_i$ in the xy coordinate system, and the second column of the transformation matrix represents $e_j$ in the xy coordinate system. On the other hand, an inverse matrix $T^{-1}$ of the transformation matrix T is a matrix in which a vector of force in the xy coordinate system is transformed into a vector of force on the coordinate system having $e_i$ and $e_j$ as basis vectors.

Next, in Step ST23, the arithmetic device 14 calculates the following magnification matrix A using the magnification factors $\alpha_i$ and $\alpha_j$ corresponding to $F_i$ and $F_j$.

$$A = \begin{pmatrix} \alpha_i & 0 \\ 0 & \alpha_j \end{pmatrix} \quad (4)$$

Next, in Step ST24, the arithmetic device 14 transforms $F_S$ into $F_P$ using the following Equation (5), and thus the linear transformation processing is finished.

$$F_P = TAT^{-1}F_S \quad (5)$$

Figure 13:
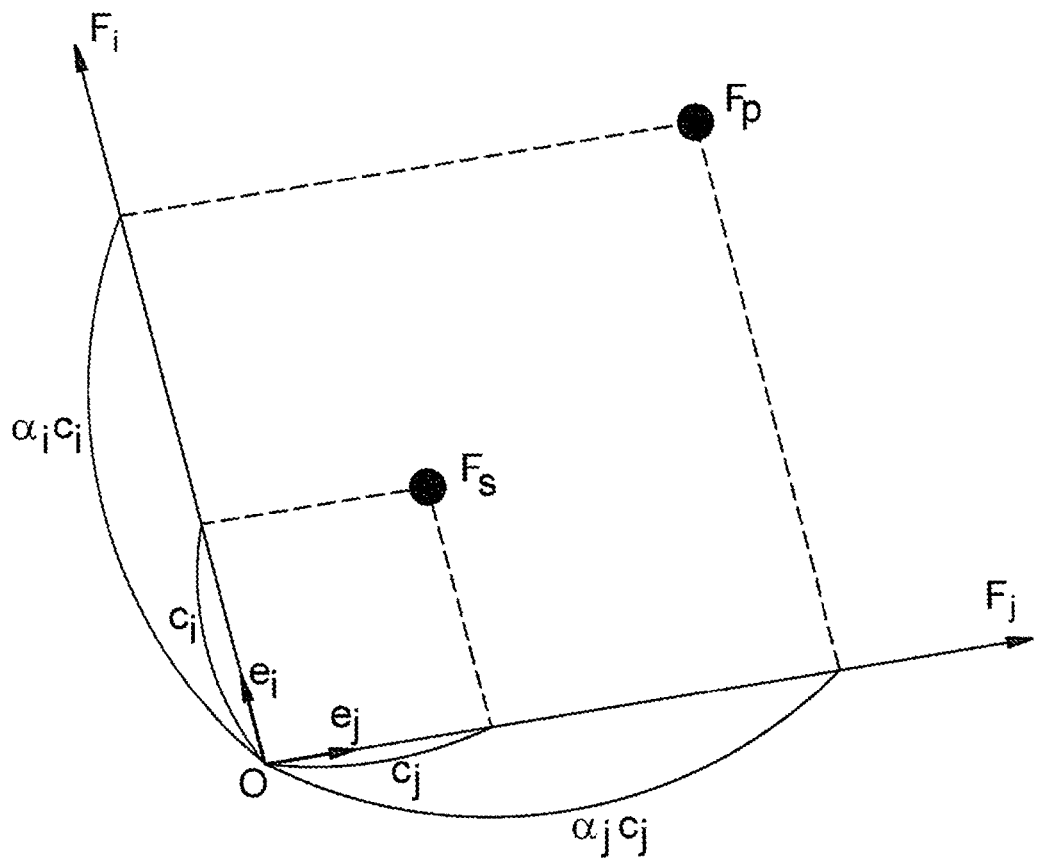
FIG. 13 is an explanatory diagram for explaining the linear transformation processing.

The vector $F_S$ of force is represented by a linear combination of $e_i$ and $e_j$ (refer to FIG. 13). More specifically, $F_S$ is represented by the sum of a vector obtained by multiplying $e_i$ by a predetermined coefficient $c_i$ and a vector obtained by multiplying $e_j$ by a predetermined coefficient $c_j$. As shown in FIG. 13, $F_P$ obtained by the above transformation equation corresponds to a vector obtained by integrating the magnification factors $\alpha_i$ and $\alpha_j$ corresponding to the coefficients. That is, $F_P$ obtained by the above transformation equation is represented by the sum of a vector obtained by multiplying $e_1$ by $\alpha_i c_i$ and a vector obtained by multiplying $e_j$ by $\alpha_j c_j$.

Although the description of the specific embodiment is finished, the disclosure can be widely modified and implemented without being limited to the above-described embodiment. The above-described embodiment is configured to include Step ST3 in which the muscle strength evaluation processing (the method for evaluating muscle strength characteristics) magnifies and corrects the orbiting output S to the maximum outputs $F_1$, $F_2$, $F_3$, and $F_4$ and calculates the magnified orbiting output P and Step ST4 in which the hexagonal maximum output distribution Q corresponding to the contribution of each muscle of the muscle group model is created based on the magnified orbiting output P but is not limited to this aspect. The muscle strength evaluation processing may include a step of creating a hexagonal maximum output distribution Q based on the maximum outputs $F_1$, $F_2$, $F_3$, and $F_4$ and the orbiting output S. For example, the muscle strength evaluation processing may include a step of calculating a hexagonal output distribution from the orbiting output S, and a step of calculating a hexagonal maximum output distribution Q by magnifying and correcting the calculated hexagonal output distribution based on the maximum outputs $F_1$, $F_2$, $F_3$, and $F_4$.

The arithmetic device 14 measures the maximum output in the four directions in Step ST1 but may measure the maximum output in at least one direction. Further, the arithmetic device 14 may be configured to calculate one magnification factor r which does not depend on a direction in Step ST3.

For example, in Step ST3, the arithmetic device 14 may extract a point A farthest from the origin O from points corresponding to the maximum output and stores a distance $L_A$ between the point A and the origin O (FIG. 14A). Next, a point B closest to an extracted point A is extracted from the orbiting output S, and a distance $L_B$ between the point B and the origin O is stored (FIG. 14B). Next, the arithmetic device 14 stores $L_A/L_B$ as the magnification factor r. Thereafter, the arithmetic device 14 may be configured so that the magnification and correction is performed by multiplying all the vectors of force included in the orbiting output S by the magnification factor r and thus the magnification orbiting output P is calculated (FIG. 14C). With such a configuration, it is possible to facilitate calculation of the magnification factor r.

In such a configuration, a magnitude of the maximum output distribution is obtained by the measurement of the maximum output, and an outline of the maximum output distribution is obtained by the measurement of the orbiting output. Thus, it is possible to reduce the number of times the subject 1 has to exert the maximum output by separately obtaining the magnitude and the outline. Therefore, even when fatigue caused by repeating the maximum output is likely to decrease the maximum output the subject 1 can exert, the maximum output distribution can be obtained with good reproducibility.

Further, in Step ST3, the arithmetic device 14 may calculate an annular approximate curve using a Bezier curve or the like based on the orbiting output S and may calculate one magnification factor r so that a distance between a magnified approximate curve obtained by magnifying a calculated approximate curve and each point of the maximum output is minimized.

In the above-described embodiment, although the method for evaluating muscle strength characteristics is used to evaluate the muscle strength characteristics of the upper limb 2 on the right side of the subject 1, it is not limited to the upper limb 2 on the right side of the subject 1 and may be the upper limb 2 on the left side of the subject 1 or any of a lower limb on the left or right side of the subject 1. Further, in the above-described embodiment, the measurement surface is set to be substantially horizontal. However, the disclosure is not limited to this aspect. For example, the measurement surface may be set to be substantially vertical. Furthermore, the method for evaluating muscle strength may be used to evaluate the muscle strength of animals such as horses, cows and dogs.

<<Other Configurations>>

According to one aspect of the disclosure, a method for evaluating muscle strength characteristics is provided. The muscle strength characteristics of a limb are evaluated based on a muscle group model including a first pair of antagonistic one-joint muscles that straddle the first joint, a second pair of antagonistic one-joint muscles that straddle the second joint, and a pair of antagonistic two-joint muscles that straddle both the first and the second joints, where the limb has a first rod having a proximal end supported by a first joint and a second rod supported on a free end of the first rod through a second joint. The method includes: measuring a maximum output of a free end of the second rod in at least one predetermined direction in a plane defined by the first and the second rods; measuring orbiting outputs of the free end of the second rod in all directions in the plane; and creating a hexagonal maximum output distribution corresponding to a contribution amount of each muscle of the muscle group model based on the maximum output in the predetermined direction and the orbiting outputs.

With such a configuration, the maximum output distribution can be obtained by magnifying the orbiting outputs based on the maximum output, and it is also possible to improve reproducibility and reliability of the maximum output distribution by combining the maximum output and the orbiting output.

In the above-described aspect, the method may further include calculating the contribution amount of each muscle of the muscle group model from the maximum output distribution.

With such a configuration, since the contribution amount of each muscle of the muscle group model is calculated, it is possible to construct a muscle group model close to the actual muscle strength characteristics of a subject. Therefore, since it is possible to identify a muscle to be reinforced, it can be used for muscle strength evaluation in rehabilitation treatments or sports.

In the above-described aspect, measuring the maximum output and measuring of the orbiting outputs may be performed in a state that the first joint and the second joint are respectively held at predetermined angles.

With such a configuration, since the angle of the first joint and the angle of the second joint are held when the maximum output and the orbiting output are measured, a subject's posture hardly changes, and the reproducibility and reliability of the maximum output distribution can be further improved.

In the above-described aspect, measuring the maximum output may be performed in each of two or more different directions, and the orbiting outputs may be magnified and corrected to the maximum output corresponding to the different directions in creating the hexagonal maximum output distribution based on the maximum output and the orbiting outputs.

With such a configuration, since a magnification factor depending on direction of the orbiting output can be set based on a plurality of maximum outputs, the magnified orbiting output can be made closer to a plurality of measured maximum outputs. Therefore, the magnified orbiting output can be made closer to the actual maximum output distribution, and the reproducibility and reliability of the maximum output distribution obtained by measurement can be enhanced.

According to the above configuration, it is possible to provide a method for evaluating muscle strength characteristics which has excellent reproducibility and reliability of an obtained maximum output distribution.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A method, implemented in a computer comprising a processor and a memory, for evaluating muscle strength characteristics, in which the muscle strength characteristics of a limb are evaluated based on a muscle group model including a first pair of antagonistic one-joint muscles that straddle a first joint, a second pair of antagonistic one-joint muscles that straddle a second joint, and a pair of antagonistic two-joint muscles that straddle the first and the second joints, where the limb has a first rod having a proximal end supported by the first joint and a second rod supported on a free end of the first rod through the second joint, the method comprising:

measuring, by a measuring device comprising a sensor, a maximum physical force of a free end of the second rod in each of two or more different directions in a plane defined by the first and the second rods based on an output of the sensor, and storing the maximum physical force in the memory;

measuring, by the measuring device, physical orbiting forces of the free end of the second rod in all directions in the plane based on an output of the sensor; and creating, by the processor, a hexagonal maximum force distribution corresponding to a contribution amount of each muscle of the muscle group model based on the maximum physical force in each of the two or more different directions and the physical orbiting forces, wherein the processor is configured to magnify and correct the physical orbiting forces to the maximum physical forces corresponding to different directions in creating the hexagonal maximum force distribution based on the maximum physical forces and the physical orbiting forces, wherein, in response to creating the hexagonal maximum force distribution, the processor is configured to control a display to display an effective muscle strength for each muscle represented by the muscle group model to notify a user a specific muscle which needs to be reinforced, wherein the measuring device comprises:

a support member having a surface;

a first link having one end coupled to the support member;

a second link having one end coupled to an other end of the first link;

a first angle sensor, configured to measure a rotation angle between the first link and the support member;

a second angle sensor, configured to measure a rotation angle between the second link and the first link;

wherein the sensor is disposed on an other end side of the second link, and wherein the sensor is configured to convert the maximum physical forces and the physical orbiting forces into electronic signals.

2. The method according to claim 1, further comprising calculating, by the processor, the contribution amount of each muscle of the muscle group model from the hexagonal maximum force distribution.

3. The method according to claim 2, wherein measuring, by the measuring device, the maximum physical force and measuring the physical orbiting forces are performed in a state where the first joint and the second joint are respectively held at predetermined angles.

4. The method according to claim 1, wherein measuring, by the measuring device, the maximum physical force and measuring the physical orbiting forces are performed in a state where the first joint and the second joint are respectively held at predetermined angles.

5. The method according to claim 1, wherein the sensor is a capacitive sensor.

* * * * *